United States Patent [19]

Leone-Bay

[11] Patent Number: 4,605,755

[45] Date of Patent: Aug. 12, 1986

[54] PREPARATION OF 1,1-DIPHENYL-2-CARBOETHOXYCYCLOPROPANE

[75] Inventor: Andrea Leone-Bay, Ridgefield, Conn.

[73] Assignee: Stauffer Chemical Company, Westport, Conn.

[21] Appl. No.: 761,987

[22] Filed: Aug. 2, 1985

[51] Int. Cl.$^4$ .............................................. C07C 69/76
[52] U.S. Cl. .................................... 560/101; 560/102
[58] Field of Search ................................. 560/101, 102

[56] References Cited

U.S. PATENT DOCUMENTS 4,157,447 6/1979 Engel .................................... 560/101

OTHER PUBLICATIONS

Tatsuno et al., "J. C. S. Chem. Comm.", (1942), pp. 588–589.
Walborsky et al., "J. Amer. Chem. Soc.", vol. 83, (1961), pp. 2517–2525.
Yanke et al., "J. Amer. Chem. Soc.", V95, (1973), pp. 4220–4230.

Primary Examiner—Werren B. Lone

[57] ABSTRACT

An improved process is disclosed for preparing racemic 1,1-diphenyl-2-carboethoxycyclopropane from 1,1-diphenylethylene and ethyl diazoacetate as reactants. It involves conducting the reaction in the absence of a metallic-based catalyst and at a reaction temperature sufficiently in excess of 60° C. to permit a yield of at least 20 percent to be obtained. Preferred conditions are given for obtaining yields in excess of 80 percent.

Related processes are also disclosed based on certain substituted 1,1-diphenylethylenes with at least one substituent in at least one phenyl group.

19 Claims, No Drawings

PREPARATION OF 1,1-DIPHENYL-2-CARBOETHOXYCYCLOPROPANE

BACKGROUND (i) Field of the Invention

This invention relates to an improved method for preparing 1,1-diphenyl-2-carboethoxycyclopropane and certain related substituted phenyl compounds. More particularly it relates to the reaction of 1,1-diphenylethylene with ethyl diazoacetate without using a metal catalyst.

(ii) Related Art

The compound 1,1-diphenyl-2-carboethoxycyclopropane (hereinafter DPCCP) has utility as an intermediate in the preparation of pharmaceuticals and other products. For example, see "Cyclopropanes and Cyclobutanes LXXII. Reactions of 1-Phenyl-2-Aminocyclopropanes with Alcohols" by Levina, R. Ya. et al. in *Zh. Org. Khim.* (1977) Vol 13, Issue 3, at pages 543–7 (hereinafter Levina). Levina discloses that the precursor DPCCP (ethyl 1,1-diphenyl-2-cyclopropanecarboxylate) was synthesized as Compound VII from 1,1-diphenylethylene and diazoacetic ester. The yield was 40%; bp 182°–185° C. (5 mm Hg). Levina refers to "Reference 9" for the method of preparation. Reference 9 is a Dissertation by A. S. Koz'min, Moscow State University (1971). The Lenin Library in Moscow was asked to sell a copy of Reference 9 but responded that it is "unavailable". A computer search indicated that Chemical Abstracts Service had not indexed any "Dissertation" by Koz'min. Accordingly "Reference 9" does not appear to be prior art.

A number of references describe the preparation of DPCCP from 1,1-diphenylethylene (hereinafter DPE) and ethyl diazoacetate (hereinafter EDZC). However, they all apparently relate to the use of a metal catalyst. For example, see "Enantioselective Synthesis of 2-Phenylcyclopropanecarboxylates through Chiral Cobalt Chelate Complex-Catalysed Carbenoid Reactions" by Tatsuno et al., *J. C. S. Chem. Comm.* (1974) at pages 588–589 (hereinafter Tatsuno). The reactions were all apparently carried out at 10° (sic) with different types of cobalt-based catalysts. Some of the cobalt catalyst systems gave optically active products; other cobalt catalyst systems gave products that were totally optically inactive or slightly active.

Essentially, nowhere does the now-known prior art disclose the use of either (1) absence of catalyst; or (2) high temperatures.

SUMMARY OF THE INVENTION

In contrast to the aforementioned art it has now been surprisingly discovered that racemic DPCCP may be prepared in good yields and high purity from DPE and EDZC without a catalyst and at high temperatures.

DESCRIPTION OF THE PREFERRED EMBODIMENTS

The conditions used in the process of this invention may be similar to those used in the prior art for preparing the same final product, except for the combination of (1) absence of catalyst; and (2) use of higher reaction temperatures.

A first preferred aspect of the invention is an improved process for preparing racemic 1,1-diphenyl-2-carboethoxycyclopropane from 1,1-diphenylethylene and ethyl diazoacetate as reactants, wherein the improvement comprises: conducting the reaction in the absence of a metallic-based catalyst and at a reaction temperature sufficiently in excess of 60° C. to permit a yield of at least 20 percent to be obtained, based on the weight of 1,1-diphenylethylene.

The term "essentially racemic" as used herein is used as characterizing a mixture of dextrorotatory and levorotatory isomers of the same compound which are present within the range from 40/60 to 60/40. The term "racemic" is limited to the mixture with equal quantities and which is optically inactive.

The first aspect of the invention is illustrated by Examples 1, 3 and 4 below, in contrast to Comparative Example 2 and the prior art.

Example 1 below is a preferred embodiment of the invention. It illustrates the preparation of racemic DPCCP by reacting DPE with an equimolar amount of EDZC at a temperature of about 115° C. for 12 hours in the absence of a catalyst. The EDZC was dissolved in an equiweight amount of dichloroethylene.

Examples 3 and 4 and Comparative Example 2 below were essentially similar to Example 1 except for the use of a different reaction temperature and resultant yield of DPCCP.

The invention is, of course, not limited to the actual working Examples below. Proposed Examples 5–9 are intended to illustrate the proposed use of a substituted DPE (hereinafter SDPE) with at least one substituent in at least one phenyl group thereby forming a substituted DPCCP (hereinafter SDPCCP). Permissible substituents include the following radicals: alkoxy; alkyl; nitro; thioalkyl; and halogen. When the substituent contains carbon, it is preferred that it contain no more than 10 carbon atoms, and more preferably less than 6 carbon atoms. Impermissible substituents include those that are significantly reactive with EDZC at elevated temperatures (such as olefinic, acetylenic, and carbonyl); and those that are self-reactive (such as aldehydic).

The optimum reaction temperature will depend in part upon the non-EDZC reactant. The upper temperature is preferably less than 200° C.; more preferably less than 175° C.; and most preferably less than 150° C. The reaction temperature is preferably greater than 80° C.; and more preferably greater than 100° C.

The molar ratio, r, of DPE (or SDPE) to EDZC is preferably in the range from 2:1 to 1:3; more preferably 1:1 to 1:2; and most preferably about 1:1.

The reaction is preferably conducted in the presence of a dispersant, which is preferably essentially inert and not volatile at the reaction temperature. Preferred dispersants include the following: tetrachloroethylene, toluene, xylenes, dichloroethylene and similar haloalkyl, aromatic and hydrocarbon solvents. Trichloroethylene is a more preferred dispersant. It is preferred that the dispersant be present in an amount of up to ten times the weight of EDZC used in the reaction; and more preferably up to four times the weight of EDZC.

The yield of DPCCP (or SDPCCP), based on DPE (or SDPE) or EDZC should be greater than 20 percent; preferably greater than 50 percent; and most preferably greater than 80 percent.

The following Examples and Proposed Examples illustrate the invention, but do not limit it. The Comparative Example is outside the invention and is not prior art.

EXAMPLE 1

This Example illustrates the preparation of 1,1-diphenyl-2-carboethoxycyclopropane in the absence of a catalyst and at a temperature in the range of 110° C.–120° C. The yield of pure product was 83%.

A 250 ml three-neck round bottom flask was equipped with a heating mantle, a magnetic stir bar, a thermometer, an addition funnel and a condensor vented to a nitrogen outlet. The flask was charged with 5 ml (28.3 mM) of diphenylethylene (DPE) and the pot contents were heated to between 110° C. and 120° C. A solution of 3.0 ml (28.3 mM) of ethyldiazoacetate (EDZC) in 3 ml of dichloroethylene was added dropwise with stirring at such a rate as to control the evolution of nitrogen, over a period of about 0.5 hours. The reaction mixture was held at 110° C.–120° C. overnight, and then worked-up by concentration in vacuo.

Distillation under reduced pressure gave 6.27 g. (83%) of 1,1-diphenyl-2-carboethoxycyclopropane (DPCCP) as a yellow oil bp 156°–158° C./0.45 mm Hg. The spectral properties of this material were identical to those reported in the literature for racemic DPCCP.

COMPARATIVE EXAMPLE 2

This Comparative Example is not prior art. It illustrates the fact that a temperature of 60° C. is too low for any significant desired reaction to proceed.

Example 1 was essentially repeated except that the reaction temperature was 60° C. instead of 115° C.

The yield of DPCCP was essentially zero.

EXAMPLE 3

Example 1 was essentially repeated except that the reaction temperature was about 100° C. (rather than 115° C.).

The yield of DPCCP was only 47% (rather than 83%).

EXAMPLE 4

Example 1 was essentially repeated except that the reaction temperature was about 150° C. (rather than 115° C.).

The yield of DPCCP was only 21% (rather than 83%).

PROPOSED EXAMPLE 5

This Proposed Example relates to the proposed use of a substituted DPE with at least one alkoxy radical as a substituent in at least one phenyl group.

Example 1 is essentially repeated except that 1-anisoyl-1-phenylethylene is substituted for an equimolar amount of DPE.

PROPOSED EXAMPLE 6

This Proposed Example relates to the proposed use of a substituted DPE with at least one alkyl radical as a substituent in at least one phenyl group.

Example 1 is essentially repeated except that 1-tolyl-1-phenylethylene is substituted for an equimolar amount of DPE.

PROPOSED EXAMPLE 7

This Proposed Example relates to the proposed use of a substituted DPE with at least one nitro radical as a substituent in at least one phenyl group.

Example 1 is essentially repeated except that 1-(p-nitrophenyl)-1-phenylethylene is substituted for an equimolar amount of DPE.

PROPOSED EXAMPLE 8

This Proposed Example relates to the proposed use of a substituted DPE with at least one thioalkyl radical as a substituent in at least one phenyl group.

Example 1 is essentially repeated except that 1-(p-thiomethylphenyl)-1-phenylethylene is substituted for an equimolar amount of DPE.

PROPOSED EXAMPLE 9

This Proposed Example relates to the proposed use of a substituted DPE with at least one halogen radical as a substituent in at least one phenyl group.

Example 1 is essentially repeated except that 1-(p-chlorophenyl)-1-phenylethylene is substituted for an equimolar amount of DPE.

What I claim is:

1. An improved process for preparing racemic 1,1-diphenyl-2-carboethoxycyclopropane from 1,1-diphenylethylene and ethyl diazoacetate as reactants, wherein the improvement comprises:

conducting the reaction in the absence of a metallic-based catalyst and at a reaction temperature from 110° C. to 150° C. to permit a yield of at least 20 percent to be obtained, based on the weight of 1,1-diphenylethylene.

2. The process of claim 1 wherein the molar ratio, r, of 1,1-diphenylethylene to ethyl diazoacetate is in a range from 2:1 to 1:3.

3. The process of claim 2 wherein r is in the range from 1:1 to 1:2.

4. The process of claim 2 wherein r is about 1:1.

5. The process of claim 1 which comprises conducting the reaction in the presence of a dispersant, the dispersant being present in an amount by weight of up to ten times the weight of ethyl diazoacetate initially present.

6. The process of claim 5 wherein the dispersant is present in an amount of up to four times the weight of ethyl diazoacetate initially present.

7. The process of claim 6 wherein the dispersant is selected from the group consisting of haloalkyl solvents, aromatic solvents and hydrocarbon solvents.

8. The process of claim 7 wherein the dispersant is dichloroethylene.

9. The process of claim 1 wherein the yield is greater than 50 percent.

10. The process of claim 9 wherein the yield is greater than 80 percent.

11. A process for preparing a racemic substituted 1,1-diphenyl-2-caraboethoxycyclopropane from ethyl diazoacetate and a substituted 1,1-diphenylethylene, SDPE, as reactants, which comprises:

conducting the reaction in the absence of a metallic-based catalyst and at a reaction temperature from 110° C. to 150° C. to permit a yield of at least 20 percent by weight to be obtained, based on the weight of the substituted 1,1-diphenylethylene.

12. The process of claim 11 wherein the SDPE comprises at least one substituent in at least one phenyl group and the substituents are selected from alkoxy, alkyl, nitro, thioalkyl, and halogen radicals.

13. The process of claim 12 wherein the SDPE comprises at least one substituent in each phenyl group and the substituents are selected from alkoxy, alkyl, nitro, thioalkyl, and halogen radicals.

14. The process of claim 12 wherein at least one substituent is an alkoxy radical.

15. The process of claim 12 wherein at least one substituent is an alkyl radical.

16. The process of claim 12 wherein at least one substituent is a nitro radical.

17. The process of claim 12 wherein at least one substituent is a methoxy radical.

18. The process of claim 12 wherein at least one substituent is a thioalkyl radical.

19. The process of claim 12 wherein at least one substituent is a halogen atom.

* * * * *